(12) United States Patent
Hossainy et al.

(10) Patent No.: US 6,979,346 B1
(45) Date of Patent: Dec. 27, 2005

(54) SYSTEM AND METHOD FOR IMPROVED STENT RETENTION

(75) Inventors: Syed Hossainy, Fremont, CA (US); Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 487 days.

(21) Appl. No.: 09/925,046

(22) Filed: Aug. 8, 2001

(51) Int. Cl.⁷ .................................................. A61F 2/06
(52) U.S. Cl. ....................... 623/1.11; 623/1.46; 623/1.15
(58) Field of Search ............................... 623/1.15, 1.44, 623/1.43, 1.46, 1.39

(56) References Cited

U.S. PATENT DOCUMENTS

| | | | |
|---|---|---|---|
| 2,701,559 | A | 2/1955 | Cooper |
| 4,323,071 | A | 4/1982 | Simpson et al. |
| 4,338,942 | A | 7/1982 | Fogarty |
| 4,439,185 | A | 3/1984 | Lundquist |
| 4,516,972 | A | 5/1985 | Samson |
| 4,538,622 | A | 9/1985 | Samson et al. |
| 4,554,929 | A | 11/1985 | Samson et al. |
| 4,573,470 | A | 3/1986 | Samson et al. |
| 4,608,984 | A | 9/1986 | Fogarty |
| 4,616,652 | A | 10/1986 | Simpson |
| 4,632,396 | A * | 12/1986 | Taylor ......................... 473/129 |
| 4,638,805 | A | 1/1987 | Powell |
| 4,702,252 | A | 10/1987 | Brooks et al. |
| 4,733,665 | A | 3/1988 | Palmaz |
| 4,748,982 | A | 6/1988 | Horzewski et al. |
| 4,869,714 | A * | 9/1989 | Deininger et al. ............ 600/36 |
| 4,880,683 | A | 11/1989 | Stow |
| 4,883,618 | A * | 11/1989 | Barrows ....................... 264/49 |
| 4,938,766 | A * | 7/1990 | Jarvik ....................... 623/3.17 |
| 4,950,227 | A | 8/1990 | Savin et al. |
| 4,994,033 | A | 2/1991 | Shockey et al. |
| 5,037,392 | A | 8/1991 | Hillstead |
| 5,059,169 | A | 10/1991 | Zilber |
| 5,064,435 | A | 11/1991 | Porter |
| 5,078,720 | A | 1/1992 | Burton et al. |
| 5,100,429 | A | 3/1992 | Sinofsky et al. |
| 5,108,416 | A | 4/1992 | Ryan et al. |
| 5,116,318 | A | 5/1992 | Hillstead |
| 5,156,911 | A | 10/1992 | Stewart |
| 5,158,548 | A | 10/1992 | Lau et al. |
| 5,226,889 | A | 7/1993 | Sheiban |
| 5,242,399 | A | 9/1993 | Lau et al. |
| 5,344,426 | A | 9/1994 | Lau et al. |

(Continued)

FOREIGN PATENT DOCUMENTS

EP      0 553 960 A1      8/1993

(Continued)

OTHER PUBLICATIONS

ACS RX MULTI-LINK™ Coronary Stent System Brochure (Undated), 7 pages.

*Primary Examiner*—Anhtuan T. Nguyen
*Assistant Examiner*—Bradford C Pantuck
(74) *Attorney, Agent, or Firm*—Fulwider Patton Lee & Utecht, LLP

(57) ABSTRACT

An implantable medical device, such as a stent, having roughened areas on an inner surface of the device for enhancing frictional contact between the medical device and a delivery system, such as a balloon catheter to secure the medical device to the delivery system during delivery of the medical device to a body lumen of a patient. Various methods for forming the roughened areas are also provided. The roughened areas may be coated with a material, such as a non-thrombogenic material, to enhance the compatibility of the inner surface of the medical device with fluid flowing through the vessel lumen of the patient.

11 Claims, 7 Drawing Sheets

U.S. PATENT DOCUMENTS

| | | | | |
|---|---|---|---|---|
| 5,360,401 | A | 11/1994 | Turnland | |
| 5,387,450 | A | 2/1995 | Stewart | |
| 5,409,495 | A | 4/1995 | Osborn | |
| 5,412,035 | A | 5/1995 | Schmitt et al. | |
| 5,445,646 | A | 8/1995 | Euteneuer et al. | |
| 5,451,233 | A | 9/1995 | Yock | |
| 5,458,615 | A | 10/1995 | Klemm et al. | |
| 5,476,476 | A | 12/1995 | Hillstead | |
| 5,496,346 | A | 3/1996 | Horzewski et al. | |
| 5,501,227 | A | 3/1996 | Yock | |
| 5,507,768 | A | 4/1996 | Lau et al. | |
| 5,514,154 | A | 5/1996 | Lau et al. | |
| 5,571,135 | A | 11/1996 | Fraser et al. | |
| 5,645,559 | A | 7/1997 | Hachtman et al. | |
| 5,653,691 | A | 8/1997 | Rupp et al. | |
| 5,667,523 | A | 9/1997 | Bynon et al. | |
| 5,695,498 | A | 12/1997 | Tower | |
| 5,700,286 | A | 12/1997 | Tartaglia et al. | |
| 5,720,726 | A | 2/1998 | Marcadis et al. | |
| 5,746,745 | A | 5/1998 | Abele et al. | |
| 5,759,474 | A | 6/1998 | Rupp et al. | |
| 5,810,871 | A | 9/1998 | Tuckey et al. | |
| 5,830,217 | A | 11/1998 | Ryan | |
| 5,836,965 | A | 11/1998 | Jendersee et al. | |
| 5,893,852 | A | 4/1999 | Morales | |
| 5,976,155 | A | 11/1999 | Foreman et al. | |
| 6,027,510 | A | 2/2000 | Alt | |
| 6,051,021 | A | 4/2000 | Frid | |
| 6,059,810 | A | 5/2000 | Brown et al. | |
| 6,063,092 | A | 5/2000 | Shin | |
| 6,066,156 | A | 5/2000 | Yan | |
| 6,086,610 | A | 7/2000 | Duerig et al. | |
| 6,099,559 | A | 8/2000 | Nolting | |
| 6,106,530 | A | 8/2000 | Harada | |
| 6,110,180 | A | 8/2000 | Foreman et al. | |
| 6,123,712 | A | 9/2000 | Di Caprio et al. | |
| 6,159,227 | A | 12/2000 | Di Caprio et al. | |
| 6,168,617 | B1 | 1/2001 | Blaeser et al. | |
| 6,174,316 | B1 | 1/2001 | Tuckey et al. | |
| 6,190,404 | B1 * | 2/2001 | Palmaz et al. | 623/1.15 |
| 6,193,727 | B1 | 2/2001 | Foreman et al. | |
| 6,206,915 | B1 * | 3/2001 | Fagan et al. | 623/1.42 |
| 6,217,586 | B1 | 4/2001 | Mackenzie | |
| 6,245,076 | B1 | 6/2001 | Yan | |
| 6,254,632 | B1 * | 7/2001 | Wu et al. | 623/1.15 |
| 6,258,099 | B1 | 7/2001 | Mareiro et al. | |
| 6,277,110 | B1 | 8/2001 | Morales | |
| 6,290,720 | B1 * | 9/2001 | Khosravi et al. | 623/1.13 |
| 6,348,060 | B1 | 2/2002 | Brown | |
| 6,395,326 | B1 * | 5/2002 | Castro et al. | 427/2.24 |
| 6,451,373 | B1 * | 9/2002 | Hossainy et al. | 427/2.25 |
| 6,558,733 | B1 * | 5/2003 | Hossainy et al. | 427/2.24 |
| 2001/0016753 | A1 | 8/2001 | Caprio et al. | |
| 2002/0114823 | A1 * | 8/2002 | Sirhan et al. | 424/423 |
| 2002/0187250 | A1 * | 12/2002 | Kokubo et al. | 427/2.1 |
| 2003/0028241 | A1 * | 2/2003 | Stinson | 623/1.15 |

FOREIGN PATENT DOCUMENTS

| | | |
|---|---|---|
| EP | 0 834 293 A1 | 4/1998 |
| EP | 0 974 315 A1 | 1/2000 |
| FR | 2 753 907 | 4/1998 |
| SU | 1477423 | 5/1989 |
| WO | WO 95/33422 | 12/1995 |
| WO | WO 98/07390 | 2/1998 |

* cited by examiner

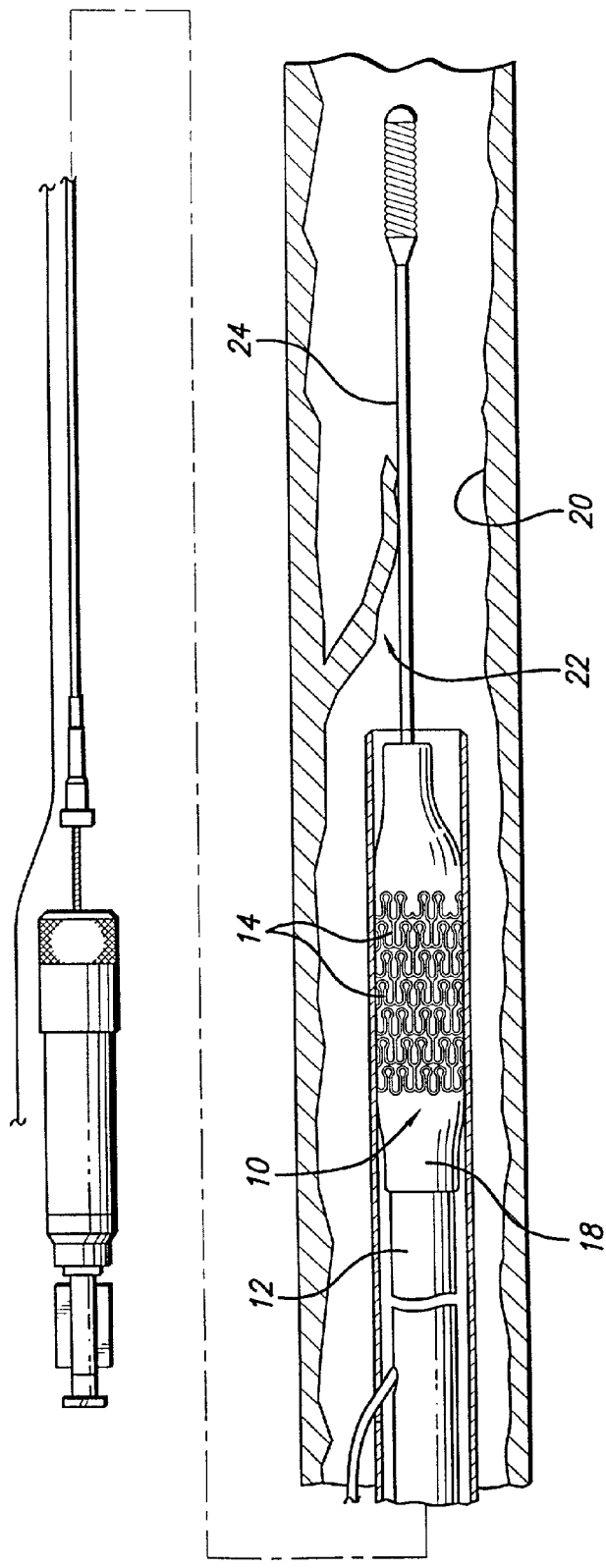
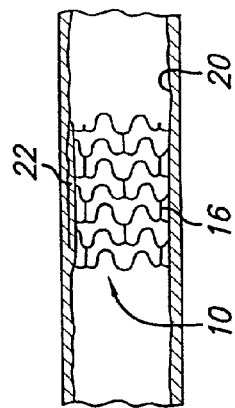
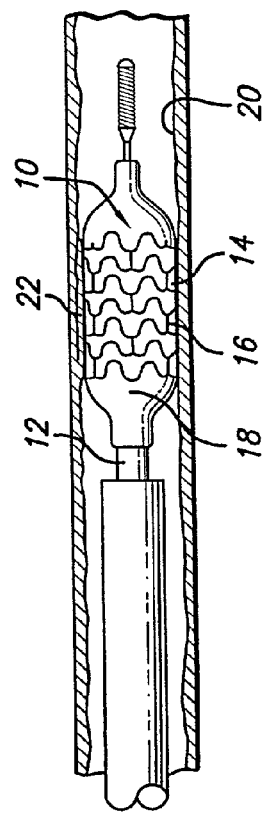
FIG. 1
FIG. 2
FIG. 3

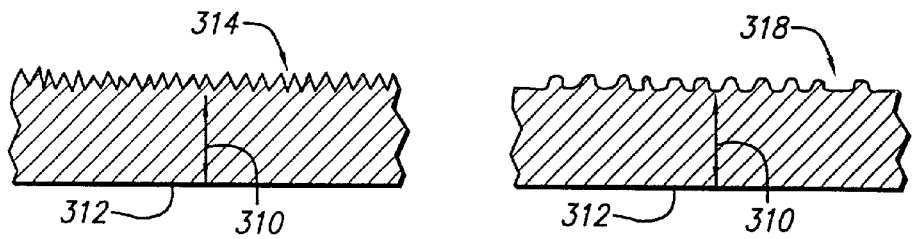
FIG. 6A  FIG. 6B
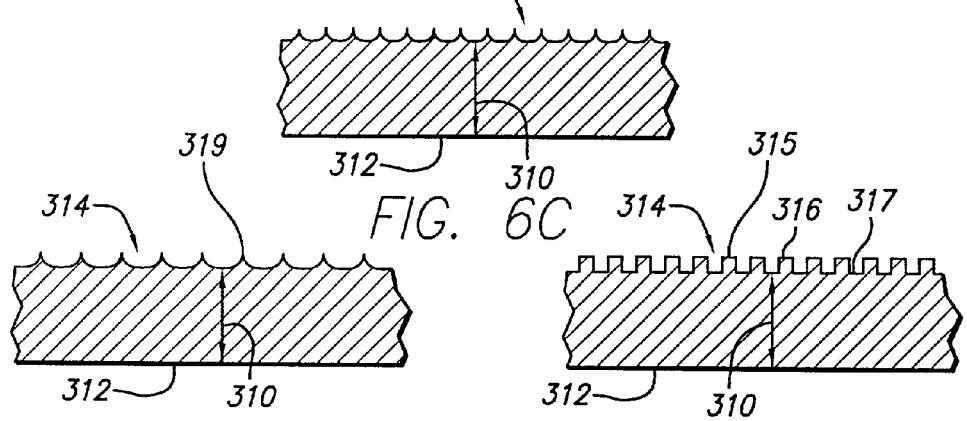
FIG. 6C
FIG. 6D  FIG. 6E
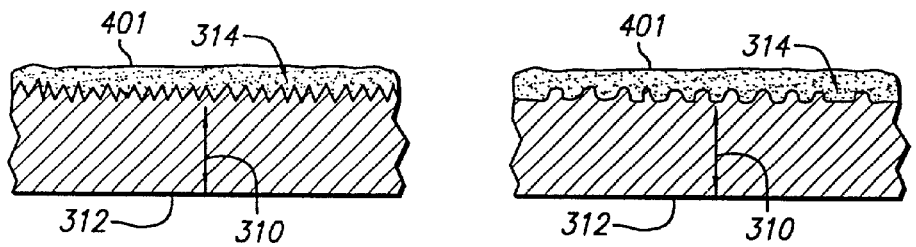
FIG. 7A  FIG. 7B
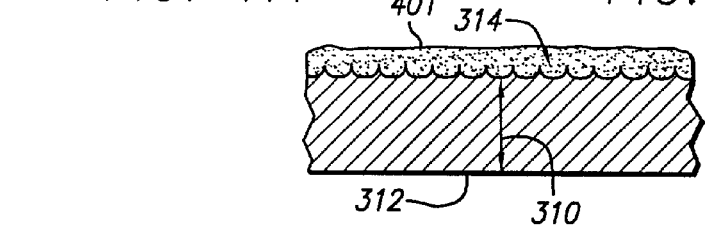
FIG. 7C
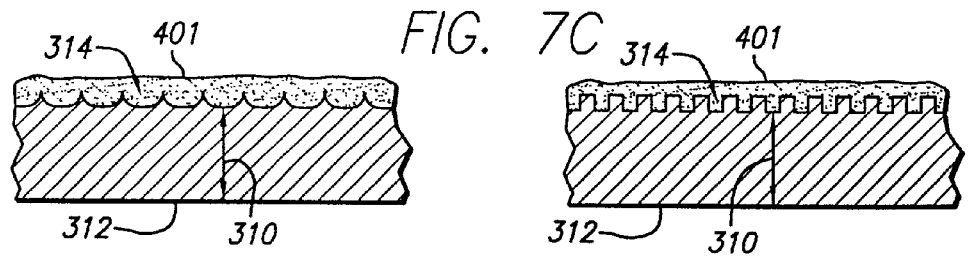
FIG. 7D  FIG. 7E

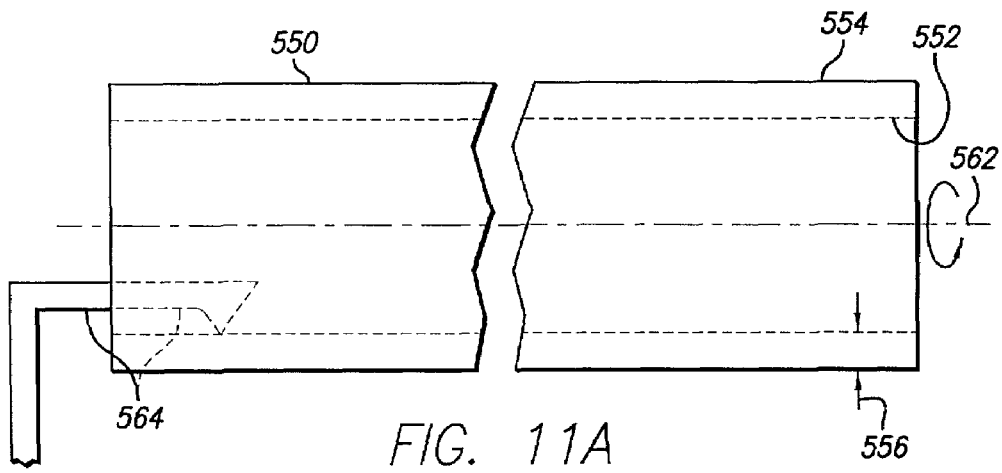
FIG. 11A
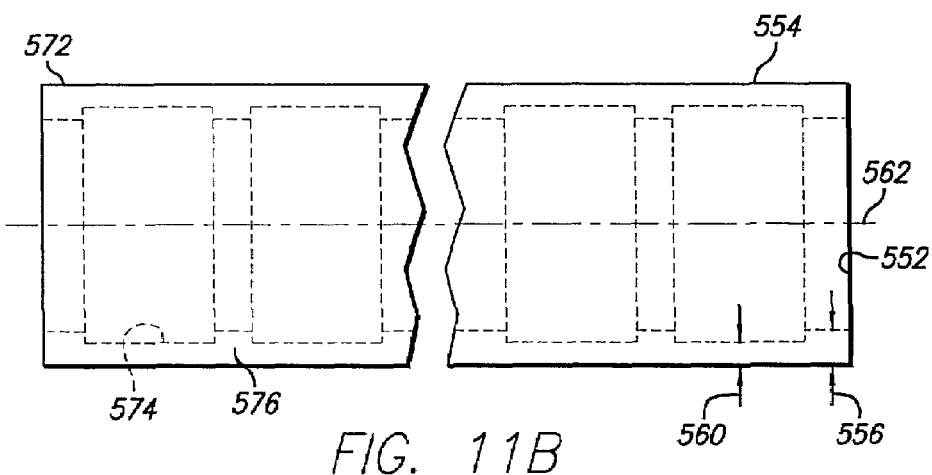
FIG. 11B
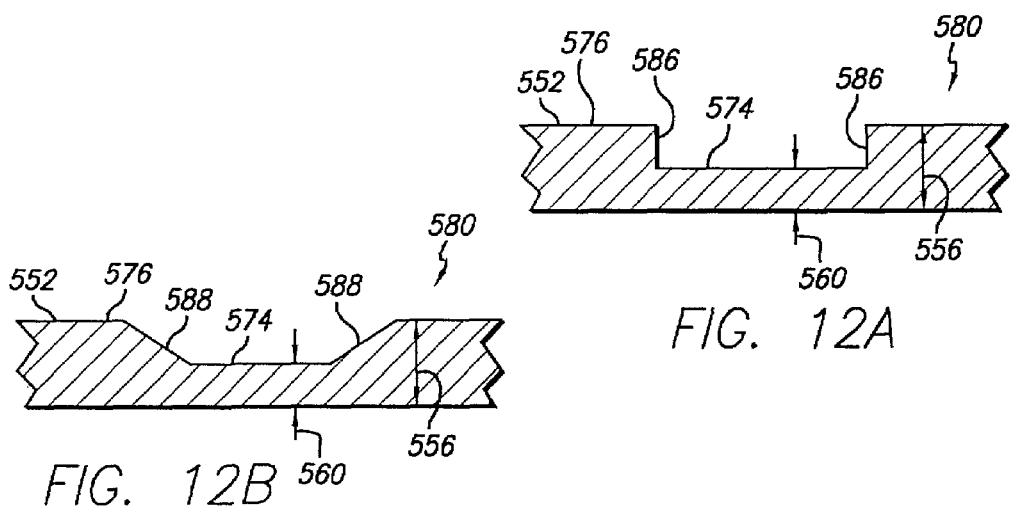
FIG. 12A
FIG. 12B

SYSTEM AND METHOD FOR IMPROVED STENT RETENTION

BACKGROUND OF THE INVENTION

This invention relates to devices for the treatment of heart disease and particularly to endo-arterial prosthesis, which are commonly called stents. More particularly, the invention relates to structures and methods for removably securing the stent to the catheter during delivery through a body lumen.

Several interventional treatment modalities are presently used for heart disease including balloon and laser angioplasty, atherectomy and by-pass surgery. In typical balloon angioplasty procedures, a guiding catheter having a pre-formed distal tip is percutaneously introduced through the femoral artery into the cardiovascular system of a patient in a conventional Seldinger technique and advanced within the cardiovascular system until the distal tip of the guiding catheter is seated in the ostium. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon, which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.), which are hereby incorporated herein in their entirety by reference thereto.

One problem which can occur during balloon angioplasty procedures is the formation of intimal flaps which can collapse and occlude the artery when the balloon is deflated at the end of the angioplasty procedure. Another problem characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices called stents. Stents are generally cylindrically shaped intravascular devices which are placed within an artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

However, retaining the position of the stent in the proper location on the expandable member while advancing the catheter through the body lumen has been found to be difficult. If the stent is dislodged from or moved on the expandable member the system will not correctly deliver the stent into the body lumen. This would require repeating the procedure. This delays insertion of the stent into the body lumen and lengthens the time of the stenting procedure.

Different methods have been attempted to maintain the position of the stent on the expandable member. One such method involves a protective sheath surrounding the catheter and stent assembly, which is retracted prior to inflation of the expandable member. The use of the sheath, however, increases the profile of the catheter assembly which must traverse narrow vessels and the sheath reduces the flexibility of the distal end of the delivery catheter. It would be an improvement to use a technique which does not increase the overall profile of the catheter assembly and maintains the flexibility of the delivery catheter.

Another method has been to remove the friction reducing coating on the expandable member in the location of the stent thereby allowing the catheter assembly's pre-coated surface to hold the stent in frictional contact. This method has not proven highly efficient in maintaining the stent in the desired location.

What has been needed and heretofore unavailable is a highly efficient means of maintaining a stent in a desired location on a stent delivery system without increasing the overall profile of the catheter assembly or compromising the flexibility. The present invention satisfies this need.

SUMMARY OF THE INVENTION

This invention is directed to an improvement in stent delivery systems for removably securing a stent onto an expandable member. Stent delivery systems are typically composed of an elongated tubular member, or catheter, encompassed by an expandable member such as an inflatable balloon. The stent is located about the expandable member so that the two can be expanded together. Securing the stent is accomplished by tightly crimping the stent onto the balloon portion of a catheter. The present invention provides an implantable medical device, such as a stent, and methods for manufacturing the same including asperities or grooves located on the side of the implantable medical device in contact with a balloon, resulting in increased frictional contact and interference between the implantable medical device and the balloon. This increased frictional contact and interference between the implantable medical device and the balloon provides for improved retention of the implantable medical device on the balloon when the catheter and implantable medical device are manipulated through a patient's vessels to a desired location where the medical device is implanted in a body lumen of the patient. The implantable medical devices of the present invention may be used with the known configurations of stent delivery catheter assemblies including over-the-wire (OTW) intravascular catheters and rapid exchange (Rx) intravascular catheters.

In one embodiment, the present invention comprises a stent having a body portion having an inner surface and an outer surface. Roughened areas are formed on selected regions of the inner surface, the roughened areas increasing the frictional contact between the inner surface of the stent when the stent is mounted on a balloon. The roughened area may include the entire inner surface of the stent, or, alternatively, only selected portions of the inner surface of the stent may be roughened. Typically, the roughened areas have a roughness factor greater than 40 nm.

In another embodiment, the roughened areas of the stent are formed by machining selected portions of the inner surface of the stent to remove material from the inner surface of the stent. The machining may be accomplished using machining tools, such as lasers or mechanical devices, or the machining may be accomplished by spraying a stream of grit, such as beads or sand, at the inner surface of the stent. Alternatively, the roughened areas may be formed by etching selected portions of the inner surface of the stent using a chemical etchant or electrochemical process. The entire inner surface of the stent may be etched, or only selected portions of the inner surface of the stent may be etched using a mask.

In yet another embodiment, the roughened area is formed on a surface of a material to the inner surface of the stent. For example, and not limited to, material may be added to the inner surface of the stent by sputtering or other means. As before, material may be sputtered onto the entire inner surface of the stent, or material may be sputtered onto selected portions of the inner surface of the stent.

In another embodiment, the roughened area is formed on a surface of a planar member of an appropriate material. The planar member may then be rolled into a tubular shape such that the surface having the roughened area forms an inner surface of the tubular shape, and a stent pattern cut into the tubular shape. Alternatively, the stent pattern may be cut into the planar member before or after the roughened area is formed on the surface of the planar member, and before or after the planar member is rolled into the tubular shape.

In yet a further embodiment, a protective material may be applied to an outer surface of a tubular body portion, or the surface of the planar member that will become an outer surface of the tubular shape, before the roughened area is formed to protect the outer surfaces from damage during formation of the roughened areas. The protective material may be removed before or after the stent pattern is cut.

In another embodiment, a coating may be applied to the inner surface of the stent after the roughened area is formed. This coating is selected to be bio-compatible and to provide reduced interaction between the roughened area of the stent and fluid flowing through a body lumen where the stent is implanted.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a stent embodying features of an embodiment of the invention which is mounted on a delivery catheter and disposed within an artery.

FIG. 2 is an elevational view, partially in section, similar to that shown in FIG. 1, wherein the stent is expanded within an artery, pressing the lining against the arterial wall.

FIG. 3 is an elevational view, partially in section, showing the expanded stent within the artery after withdrawal of the delivery catheter.

FIGS. 6A–6E are partial cross-section views of a close-up portion of a stent depicting various embodiments of asperities formed on the surface of the stent in accordance with the present invention.

FIGS. 7A–7E are partial cross-sectional views of a close-up portion of a stent showing a coating covering various embodiments of asperities formed on the surface of the stent in accordance with the present invention.

FIGS. 11a and 11b are side views, partially in phantom, depicting a stent being manufactured in accordance with an embodiment of the invention to form grooves on an inner surface of the stent.

FIGS. 12A and 12B are cross-sectional views of a portion of a stent having grooves formed on the inner surface of the stent in accordance with various embodiments of the invention.

DETAILED DESCRIPTION OF THE PREFERRED EMBODIMENTS

Figure 4:
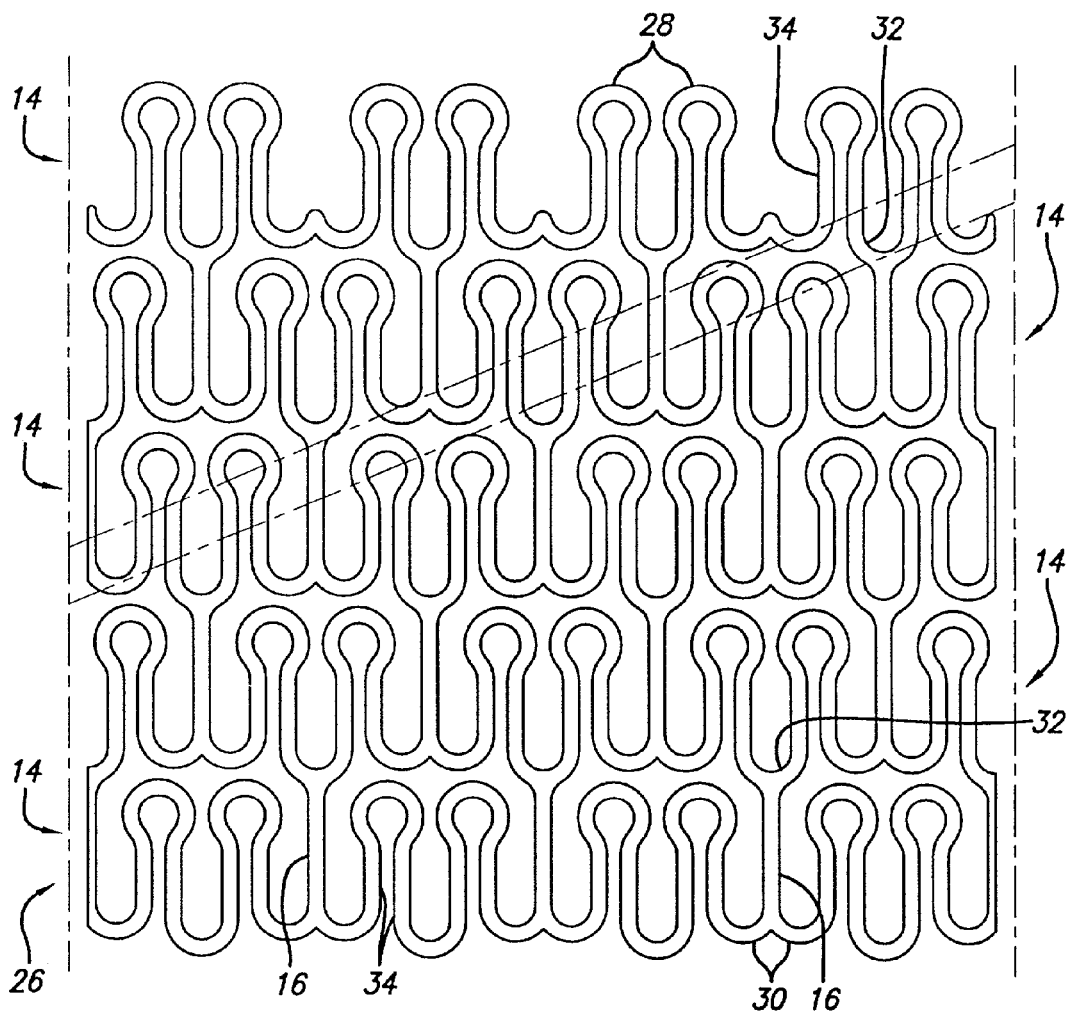
FIG. 4 depicts a stent pattern from the stent embodiment of FIG. 1.

The present invention is depicted in FIGS. 1–14B for use in various body lumens and procedures, including use in dilated arteries during balloon angioplasties. However, the present invention is not limited to use in blood vessels or angioplasties, but can be used in other body lumens and procedures, including treatment of urinary, digestive, or bile ducts.

The stent of the preferred embodiment is generally delivered intraluminally using a conventional balloon catheter as is known in the art. The stent is used primarily to ensure the patency of the body lumen in which it is implanted. For example, the stent may be implanted in the coronary arteries after an angioplasty procedure to reinforce the artery against recoil or to tack up a dissection in the arterial wall. The stent is useful for implanting in other body lumens, such as the carotid arteries, illiacs, cerebral vasculature, and other peripheral veins and arteries.

FIG. 1 illustrates a stent 10, incorporating features of the invention, which is mounted on a delivery catheter 12. The stent 10 in the embodiment depicted comprises a plurality of radially expandable cylindrical elements 14 disposed generally coaxially and interconnected by links 16 disposed between adjacent cylindrical elements 14. The delivery catheter 12 has an expandable portion or balloon 18 for expanding the stent 10 within coronary artery 20. The artery 20, as shown in FIG. 1, has a dissected lining 22 which has occluded a portion of the arterial passageway.

The delivery catheter 12 onto which the stent 10 is mounted is essentially the same as a conventional balloon dilatation catheter for angioplasty procedures. The balloon 18 may be formed of suitable materials such as polyethylene, polyethylene teraphthalate, polyvinyl chloride, nylon and ionomers such as Surlyn® manufactured by the Polymer Products Division of the Du Pont Company. Other polymers may also be used.

In order for the stent 10 to remain in place on the balloon 18 during delivery to the site of the damage within the artery 20, the stent 10 is compressed onto the balloon. Other means for securing the stent 10 onto the balloon 18 may also be used, such as providing a covering sheath over the stent, or providing collars or ridges on the ends of the working portion, i.e., the cylindrical portion, of the balloon. Thermal and/or pressure processes can also be used to secure the stent to the balloon.

The delivery of the stent 10 is accomplished in the following manner. The stent 10 is first mounted onto the inflatable balloon 18 on the distal extremity of the delivery catheter 12. The balloon 18 is slightly inflated to secure the stent 10 onto the exterior of the balloon. The catheter-stent assembly is introduced within the patient's vasculature in a conventional Seldinger technique through a guiding catheter (not shown). A guidewire 24 is disposed across a stenosed area or the damaged arterial section having a detached or dissected lining 22, and then the catheter-stent assembly is advanced over a guidewire 24 within the artery 20 until the stent 10 is directly under the detached lining 22. The balloon 18 of the catheter is expanded, expanding the stent against the artery 20, which is illustrated in FIG. 2. While not shown in the drawing, the artery 20 may be expanded slightly by the expansion of the stent 10 to seat or otherwise fix the stent 10 to prevent movement. In some circumstances during the treatment of stenotic portions of an artery, the artery may have to be expanded in order to facilitate passage of blood or other fluid therethrough.

In a preferred embodiment, stent 10 serves to hold open the artery 20 after the catheter 12 is withdrawn, as illustrated by FIG. 3. The cylindrical elements 14 of stent 10 which are pressed into the wall of the artery 20 will eventually be covered with endothelial cell growth which further minimizes blood flow interference. The undulating portion of the cylindrical sections 14 provide good tacking characteristics to prevent stent movement within the artery. Furthermore, the closely spaced cylindrical elements 14 at regular intervals provide uniform support for the wall of the artery 20.

The stent pattern 26 from the stent 10 of the embodiment of FIGS. 1–3 is depicted in greater detail in FIG. 4. The stent pattern 26, which is depicted two-dimensionally as if the tubular stent were cut longitudinally and "unrolled" to form a flat sheet, includes a series of Us, Ws, and Ys that, in combination, define a stent 10 having a series of cylindrical elements 14 connected by links 16 disposed between adjacent elements.

The conventional practice of having highly polished implantable medical device surfaces to minimize interference between the device surface and the flow of fluid within a vessel lumen contributes to poor adhesion of the stent 10 to balloon 18. The present invention improves upon previous methods of retaining stent 10 on balloon 18 as the balloon 18 and stent 10 are threaded through a patient's vasculature by providing a roughened inner stent surface to increase the frictional contact between the expandable stent 10 and the outer surface of the balloon 18.

In one embodiment of the present invention, the roughened inner stent surface is achieved by creating asperities on a designated region or regions of the surface of the stent 10. The asperities cause the designated region to have a roughness factor, Ra, defined below, greater than about 40 nm (nanometers), which is the upper limit of roughness factors typical of polished stent surfaces. Typically, the asperities so formed cause the designated region to have a roughness factor, Ra, greater than about about 100 nm.

Figure 5:
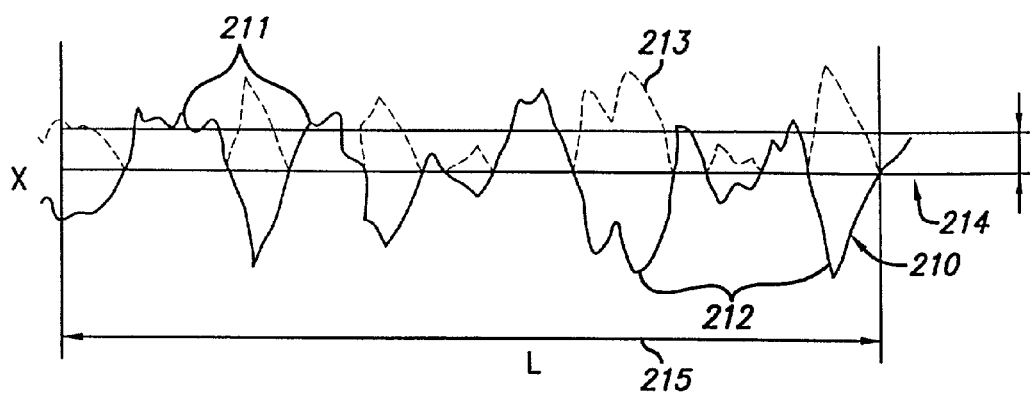
FIG. 5 is a graph of the surface of a stent having asperities formed thereon in accordance with embodiments of the present invention.

A roughness factor, Ra, is used to quantify the surface roughness. In FIG. 5, a surface having asperities is outlined in two-dimensions by the profile 210. Profile 210 outlines the irregular protrusions 211 and indentations 212 of a surface having asperities. The roughness factor, Ra, is defined herein as the arithmetic mean of the absolute values of the profile departures 213 from a centerline 214 through profile 210, within an evaluation length 215. For a three-dimensional surface, centerline 214 becomes a mean plane and Ra is defined as the arithmetic mean of the absolute values of the surface departures from the mean plane within an evaluation area. The digital approximation fort he three-dimensional Ra over an evaluation area is given as:

$$R_a = \frac{1}{MN} \sum_{j=1}^{M} \sum_{i=1}^{N} |Z_{ji}| \qquad \text{Equation 1}$$

where M and N are the number of data points in the X and Y directions, respectively, of the evaluation area, and Z is the surface height of each point relative to the mean plane.

The roughness factor, Ra, of asperities on a stent incorporating an embodiment of the present invention may be measured, for example, by using a commercially available Veeco Metrology Group (Tucson, Ariz.) WYKO NT-2000 system, which is a non-contact optical profiler. VSI (vertical scanning interferometer mode is used. For cylindrical devices, such as stents, cylinder and tilt terms are removed so that the stent surface appears flat. A low pass filter is used which removes the effects of high spatial frequency roughness, smoothing over features that are smaller than a nine pixel window. A 50× objective and 2.0× FOV converter sensor are used to provide an effective magnification of 100×. This objective and converter combination profiles a 0.58 μm×0.44 μm evaluation area, at a spatial sampling interval of 159.13 nm. For statistical purposes, samples are measured at five separate locations. Equation 1 is used to calculate a value of Ra.

In general, surface asperities in accordance with an embodiment of the present invention may have a variety of shapes, some examples of which are illustrated in FIGS. 6A–6E, showing cross-sectional views of portions of stents with average thicknesses 310 and outer surfaces 312. Inner surface asperities 314 can be random and irregular, as exemplified in FIGS. 6A and 6B. The asperities 314 can also be more regular and well-defined, as exemplified in FIGS. 6C–6E. The asperities of the various embodiments of the invention may be formed by protrusions and indentations in the surface that can have a variety of shapes and sizes, for example, the rounded shape 318 of FIG. 6B, the pointed shape 319 of FIG. 6D or the rectangular shape of 315 of FIG. 6E. Moreover, as depicted in FIG. 6E, the protrusions and indentations of the asperities formed on the surface cause the surface to have ridges 316 and channels 317. The protrusions and indentations may also have different densities on the surface, as illustrated by the difference between FIGS. 6C and 6D, depending on the requirements of the stent designer.

As shown in FIGS. 7A–7E, compatibility of the asperities located on the inner surface of the stent with fluid flowing through the stent may be enhanced by coating the asperities with a coating 401. The coating may fully cover the asperities or the peaks of the asperities may extend through the coating. The coating may comprise, for example heparin or some other non-thrombogenic material. The coating may also cooperate with the asperities to enhance the frictional contact between the stent and the balloon.

In general, the asperities may be added to the inner surface of the stent at any point in the stent manufacturing process, provided that subsequent processing does not remove the asperities. For example, the asperities on the inner surface of the stent may be created after the stent has been polished. The outer surface of the stent may be masked with a temporary protective coating, or other means for covering the outer surface of the stent, so that application of the asperities to the inner surface of the stent does not result in application of asperities to the outer surface of the stent. Alternatively, asperities may be allowed to be applied to both the inner and outer surfaces of the stent.

In on embodiment of a method according to the present invention, a poly vinyl alcohol (PVA) solution, for example, 80% by weight dissolved in hot water at 100 degrees centigrade, may be applied to the outer surface of the stent and allowed to air dry, and can be removed after application of the asperities by soaking the stent in water. In another embodiment, the asperities are created before the stent pattern is cut. In such an embodiment, the asperities must be preserved during subsequent processing of the stent. If subsequent processing might destroy or remove the asperities, a temporary coating, as described above, may be applied to the outer surface of the stent to preserve the asperities.

Figure 8:
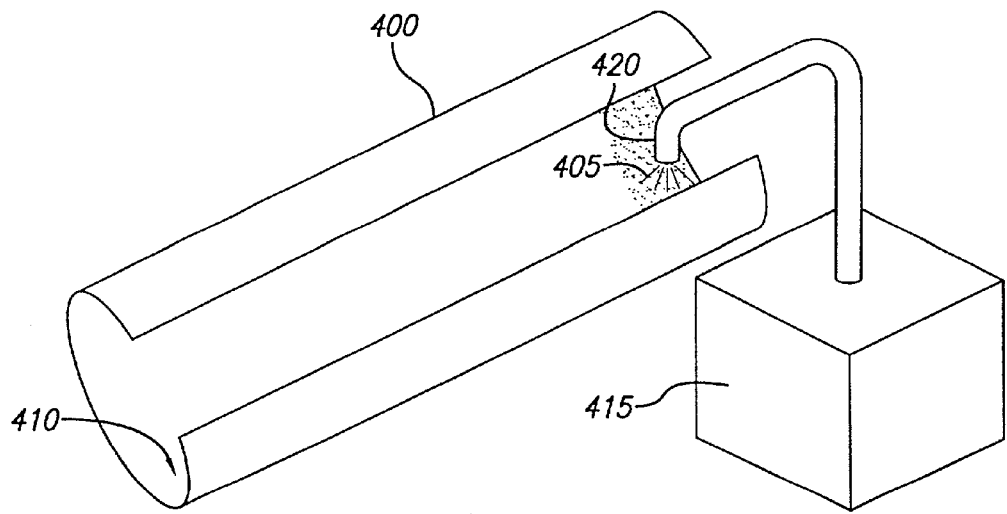
FIG. 8 is a partial cross-sectional view of a stent showing an inner surface of the stent being machined to form asperities on the inner surface of the stent in accordance with one embodiment of the present invention.
Figure 9:
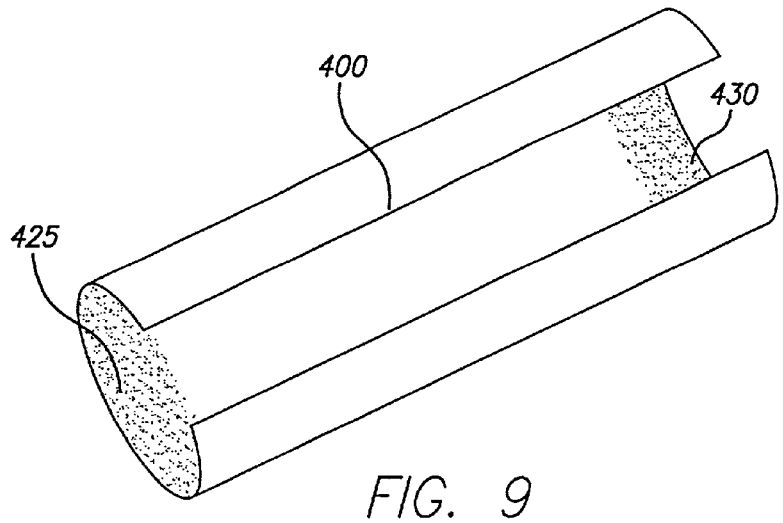
FIG. 9 is a cross-sectional view of the stent of FIG. 8 having asperities formed on end portions of the stent.

A variety of methods can be used to create the asperities on the inner surface of the stent. FIG. 8 illustrates one embodiment, in which a pressurized stream of grit material 405 is directed upon the inner surface 410 of stent 400 by a pressure spray device 415, such as a bead or sand blaster, and a nozzle or an aperture 420, to create asperities on the inner surface of the stent. The entire inner surface of the stent need not be roughened. For example, as illustrated in FIG. 9, the grit may be projected at only the end regions 425, 430 of the stent 400. Examples of such processes include bead blasting and sand blasting. Bead blasting refers to the use of pressurized gas to project beads of a relatively uniform diameter at an object at a high velocity. The bead may be made of a variety of materials, such as latex, aluminum oxide, or silicon oxide. In sand blasting, the grit projected does not have as uniform a diameter as bead blasting. Both bead blasting and sand blasting are techniques that are well known in the art.

The roughness factor achieved using a pressurized grit source can be controlled by the size of the grit, e.g., the diameters of the beads, the pressure used, the distance between the grit source and the stent surface, and the length of time the grit is blasted at the surface. By way of example and not limitation, the grit may be beads having a diameter of between 10 $\mu$m and 50 $\mu$m. Pressures of 30 pounds per square inch (PSI) can be used to project the grit at the surface of the stent. Average roughness values achieved are typically in a range of 100 nm to 200 nm, and preferably in a range of 130 nm to 210 nm.

In another embodiment, chemical etching is used to create asperities on the inner surface of the stent. Chemical etching methods are known to those of ordinary skill in the art. The chemical etchant solution typically includes an acid that degrades and dissolves the material from which the stent is made. The chemical etchant is applied to the inner surface, and then rinsed off of the surface after a predetermined period of time. The length of time the etchant is left on the surface depends on the etch rate and the depth of etch desired.

The roughness factor produced by the chemical etchant depends on the method of application of the etchant. In one embodiment, a temporary protective coating, e.g., polyvinyl alcohol dissolved in water, may be applied to the outer surface of the stent to protect the outer surface from the etchant to keep the outer surface smooth. Alternatively, both inner and outer surfaces of the stents may be roughened using the etchant. The chemical etchant is rinsed off of the stent, leaving a rough inner surface. The roughness factor will depend on the stent material and the chemical etchant used, the amount and length of time the etchant was applied, and how the etchant was applied.

In one embodiment, the stent is made of a composite material where one of the components of the composite material can be easily dissolved by the chemical etchant. For example, a metal alloy, such as stainless steel can be used to form the stent and nitric acid can be applied to the inner surface to create asperities thereon. A hydrochloric acid solution, 37 percent by volume and water can also be used to create the asperities.

In another embodiment, a patterned mask that has openings may be applied to the stent inner surface before the chemical etchant is applied. The etchant is then applied in a uniform manner and allowed to etch the stent material through the openings of the mask. The use of a patterned mask with chemical etchants is known to those of ordinary skill in the art. Because it is usually easier to mask and etch a flat piece of material than the inner surface of a hypo-tube, the mask is typically applied to a flat piece of the stent material and the resulting inner surface pattern etched into the surface. The flat piece of stent material may then be cut, rolled, and joined into a stent. The flat piece of stent material may be polished before the mask and etch process, so that the asperities created by the mask and etch are not the degraded in subsequent polishing processes. Additionally, a cutting process that does not leave scrap between the stent struts can be used to eliminate a descaling step to remove such scrap which may also damage the asperities. For example, the stent patterns may be cut using another chemical etching step where the second mask which protects the asperity is in the pattern of the stent and the etchant is allowed to dissolve all material not masked.

In this embodiment, the pattern mask can be used to make asperities that are composed of more regular and well-defined shapes. The shapes can be chosen depending on the eventual application of the stent. In one example, pattern masking followed by etching is used to create asperities composed of relatively sharp tips (319 of FIG. 6D), or ridges and channels (315 and 317, respectively, of FIG. 6E). The sharp tip 319 can have a height between 0.1 micrometers and 10 micrometers. The sharp tips can be of any density on the surface, although a higher density produces more surface etch area, providing better mechanical frictional contact with the outer surface of a balloon. The asperities made by this method typically have roughness factor between 50 nanometers and 5 micrometers.

If, when creating the asperities by chemical etching, a significant amount of stent material will be removed, for instance, to reduce the average thickness of the stent strut by more than 10 percent, a thicker material can be used to form the stent. Therefore, the finished stent has the desired strut thickness after etching so that the structural integrity of the stent is not compromised by creating the asperities.

In still a further embodiment, the stent may be formed from a sheet of material having an inner surface measurably rougher than the outer surface of the stent. In this embodiment, selected portions of the inner surface of the stent are polished, leaving portions of the finished stent with areas that are measurably rougher than the polished areas. Similarly, where a flat sheet of material is rolled to produce a stent blank, the side of the flat sheet that is to become the inner surface of the stent may be measurably rougher than the side of the sheet that is to become the outer surface of the stent. As described previously, selected portions of the flat sheet may be polished before or after the sheet is rolled into a hollow tube form which the stent is cut, yielding a hollow tube having smoother portions and rougher portions, as required by the designer of the stent. Similar to the other embodiments described above, the rougher surface may be protected during further processing, such as polishing of the outer surface and/or selected portions of the inner surface of the stent, by a coating or other means to preserve the rougher surface.

In yet another embodiment, additional material may be deposited onto the inner surface of the stent to create the asperity. In one method, the additional material, which is typically a metal, is first made into a powder. The powder particles are then bonded to the inner surface to form the asperity. The powder can be made, for example, by grinding the metal to form particles of a predetermined size. The particles are then-put onto the inner surface of the stent, for example, by spraying the powdered metal onto the inner surface of the stent. The stent can be electrostatically charged to a charge, typically negative, that is opposite that of the powdered metal, to improve the adhesion of the powder to the stent.

The stent coated with the particles is then heated to weld the particles to the stent by methods known to those skilled in the art, such as, for example, by sintering the coated stent in a furnace or with a flame. Typically the stent material, particle material, and sintering temperature are chosen so that melting temperatures of the materials allow the particles to be welded to the stent without distortion of the stent by the heat treatment. For example, the stent material may be 316L stainless steel and the particles may be gold aluminum or copper. The sintering temperature is chosen to be below the melting temperature 316L stainless steel, approximately 1388° C.

In this method, the outer surface of the stent may be protected by applying a temporary coating to the outer surface, or otherwise covering the outer surface, to prevent the particles from contacting and staying on the outer surface when they are applied to the stent. The coating, typically a polymeric material will burn off of the stent in the subsequent heat treatment to sinter the particles to the stent material. The temporary coating can also be used on the inner surface of the stent if it is desired to create asperities on only designated regions of the inner surface. For example, if it is desired to have the asperities adjacent to the ends of the stent, as illustrated in FIG. 9, the temporary coating can be applied to the middle portion of the stent before the particles are applied to the stent. As described above, while such procedures may be performed on a rolled stent, it is also possible to use such methods to coat the surface of a flat sheet of stent material that is intended to form the inner surface of the completed stent.

The roughness factor, Ra achieved using this method depends on the size of the particles and powder and is usually in the range of 50 nanometers to 5 micrometers.

Figure 10:
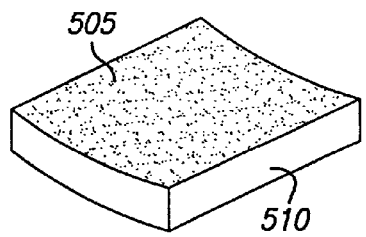
FIG. 10 is a perspective elevational view of a portion of an inner surface of a stent depicting asperities formed on the inner surface by means of an embodiment of the present invention.

The additional material may also be added to the inner surface of the stent by a physical deposition processes, such as, for example, sputtering, which known to those of ordinary skill in the art. In sputtering an energy beam, for instance, an ion beam, is directed at a target formed of the material which is to be deposited on the substrate. The energy beam dislodges atoms of the target material. The target material atoms are transported to the substrate which in this instance is the stent on which the asperities are being formed. Once at the substrate the atoms form "islands," or small nodules of the deposition material on the substrate. FIG. 10 illustrates the "islands" 505 formed on an illustrative portion of the inner surface of the stent 510.

Conventionally, sputtering is used to form a thin film of the deposition material over the substrate, and sputtering conditions are used such that the "islands" grow, spread, and condense on the substrate to form a thin film. To form asperities, however, the sputtering process conditions are set so that instead of creating a uniform film over the substrate the "islands" do not grow, spread, and condense leaving a rough surface. Process conditions in which a lower pressure and shorter deposition times than are typically used for thin film deposition are used to form the asperities.

Typically, the outer surface of a cut stent is coated with protective material before being exposed to the sputtering process to prevent adhesion of the sputtered materials to the outer surface of the stent. As described above, the protective coating may also be applied to selected portions of the inner surface of the stent to protect those selected areas, and thus form asperities only in the regions of the stent that are not so protected. Alternatively, the material can be deposited onto the inner surface of a hypo-tube before the stent pattern is cut into it, or onto a flat piece of stent material before it is cut and rolled into a stent. If the subsequent processing of the stent may destroy the added asperities, a temporary protective coating may be applied to protect them.

The sputtering process, however, may only loosely deposit the material onto the inner surface of the stent. In such cases, to further enhance attachment of the deposited material to the substrate, a heat treatment, for instance, sintering, can be performed. As discussed above, the temperature ranges for heating will depend on the deposition material and the stent material. The roughness factor achieved in this embodiment will have a lower value of approximately 50 nanometers, and an upper value of approximately 200 nanometers.

Typically, material is added to the inner surface of the stent after the stent is polished although it can be done at any point in the stent manufacturing process provided the subsequent processes do not remove the asperities. This will again depend on the material that is used to manufacture the stent and the material deposited on the stent.

In another embodiment, radiopaque materials may be deposited on the stent to not only create asperities on the stent, but also to allow improved visualization of the stent after implantation. For example, the radiopaque material can be applied adjacent to the ends of the stent.

In other embodiments, asperities may be performed by machining or laser cutting the inner surface of the stent. These methods can also be used to make asperities composed of more regular and well-defined shapes. For example, a laser discharge machine tool can be programmed to cut a desired pattern into the inner surface of a stent. Because machining and laser cutting will typically remove material from the stent, a thicker material can be used to form the stent, resulting in a completed stent having the desired average strut thickness. While it is possible to use machining and laser cutting techniques to create asperities on the inner surface of a hypo-tube that is to be cut into a stent pattern, such techniques are easier to perform and provide more uniform results on flat sheet that is then cut, rolled, and joined into a stent. The stent pattern may be cut into such a sheet material either before or after rolling the stent.

In another embodiment of the present invention, grooves or other forms of controlled roughening may be applied to the inner surface of the stent, thus increasing the frictional contact between the expandable stent and the outer surface of the balloon 18 (FIGS. 1–2).

Due to manufacturing and other considerations, it may be desirable to start with a rough stent form having a desired larger-than-nominal thickness, and then selectively reducing the thickness of desired portions, such as the flexing portions, to a nominal thickness. In the embodiment depicted in FIG. 11A, a rough tubular section 550 is depicted having a greater-than-nominal thickness 556. Material is removed from selected portions 574 of the inner surface 552 of rough tubular stent form 550, which in the embodiment depicted in FIG. 11B involves machining, until a nominal thickness 560 is achieved. In the embodiment of FIG. 11B, the machining involves rotating the rough tubular section 550 about its longitudinal axis 562, such as may be accomplished using a lathe or other rotating device, and pressing a machining tool 564 against inner surface 552. Other techniques can also be used within the scope of the invention to remove the material, including chemical etching, laser ablation, centerless grinding, and/or milling.

The result is a variable-thickness tubular section 554 having thicker areas 576 of the original greater-than-nominal thickness and thinner areas 574 with nominal thickness, as depicted in FIG. 11B. Next, the stent pattern, for example, the pattern depicted in FIG. 4, is cut into the tubular section 550.

The above-cited steps may be conducted in a different order. For example, a stent pattern could be cut into a rough tube prior to the step of reducing the thickness of the flexible portions.

In addition to the physical machining methods outlined above, the reduction in thickness can be achieved through a variety of other methods, including ablating the selected surface areas. The ablation could be performed through various methods, including chemical and/or laser ablation. This step may also be performed as part of the process of cutting the stent pattern into the rough stent form. For example, where laser cutting is used to cut the stent pattern, the laser might also be used to thin desired portions of the rough stent form. Such thinning using a laser might involve changing the focus depth of the laser or changing the laser power. Depending on the desired stent pattern, the laser and stent are moved relative to each other to generate the desired pattern. For example, the stent may be moved in any direction and/or rotated in any direction relative to the laser beam in order to achieve a desired result. Note that the stent itself does not have to physically moved if the laser beam is instead moved to cause a net result of stent movement relative to the laser beam.

It may be desirable to provide gradual transitions between areas of nominal and less-than-nominal thickness. For example, FIG. 12A shows a close-up, in cross-section, of a portion of the wall section 580 of the rough tubular form 550 shown in FIG. 11B. As depicted in FIG. 12A, the inner surface 552 has borders 586 that are well-defined between the thinner areas 574 of thickness 560 and the thicker areas 576 of thickness 556. In another embodiment depicted in FIG. 12B, the inner surface 552 has a more gradual transition region 588 between the thinner areas 574 and the thicker areas 576. Thus, the inner surface 552 of the rough tubular form 550, and the resulting finished stent, is free of sharp drop-offs between adjacent areas, and instead has gradual ramping transition regions 588 that provide a smoother transition between adjacent areas. The gradual transition regions are not required to be formed as straight ramps, but may be formed in a variety of simple and/or complex geometrical shapes, depending on the particular application. Such transition regions are useful in that they provide increased frictional contact between the inner surface of the stent and a balloon without using abrupt contours or sharp edges that may damage the balloon when the stent is crimped onto the balloon, or when the balloon is inflated to deliver the stent to a vessel lumen.

As stated previously, the sloping of such areas can range from simple sharp cutoffs to any number of complex geometric patterns. Moreover, the invention is not limited to any particular geometry at any particular site on the stent. Various geometries may be used on a single stent. The geometries may vary across particular sites on the stent to enhance desired characteristics at the particular sites. Various geometries may also have potentially therapeutic benefits in avoiding vessel trauma during stent delivery and/or deployment, as well as engineering benefits such as improved fatigue and strength properties from using the smooth transitions.

Figure 13A:
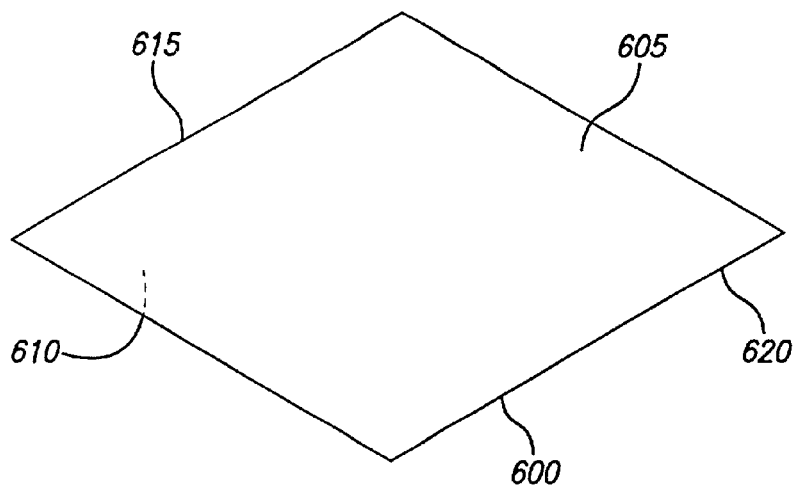
FIGS. 13A, 13B, and 13C are perspective views of a stent being manufactured in accordance with an embodiment of the invention.
Figure 13B:
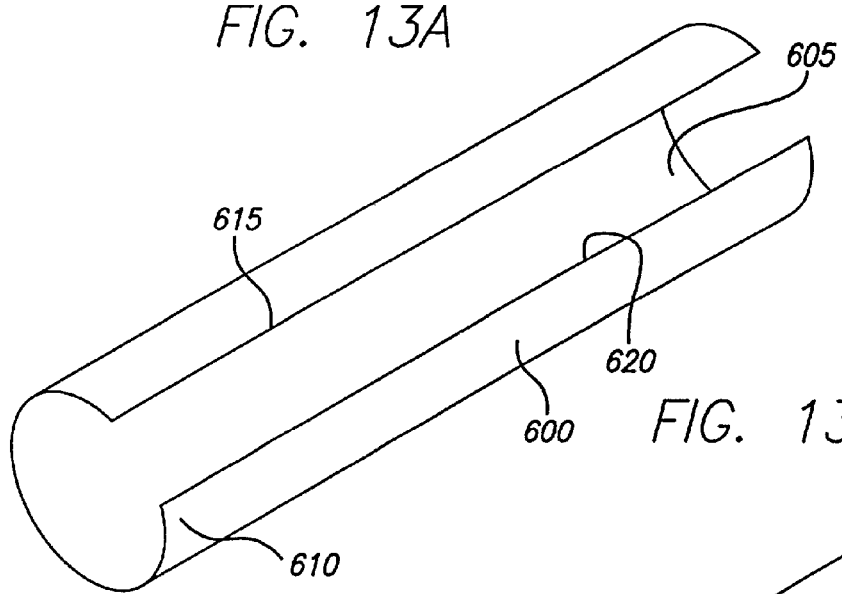
Figure 13C:
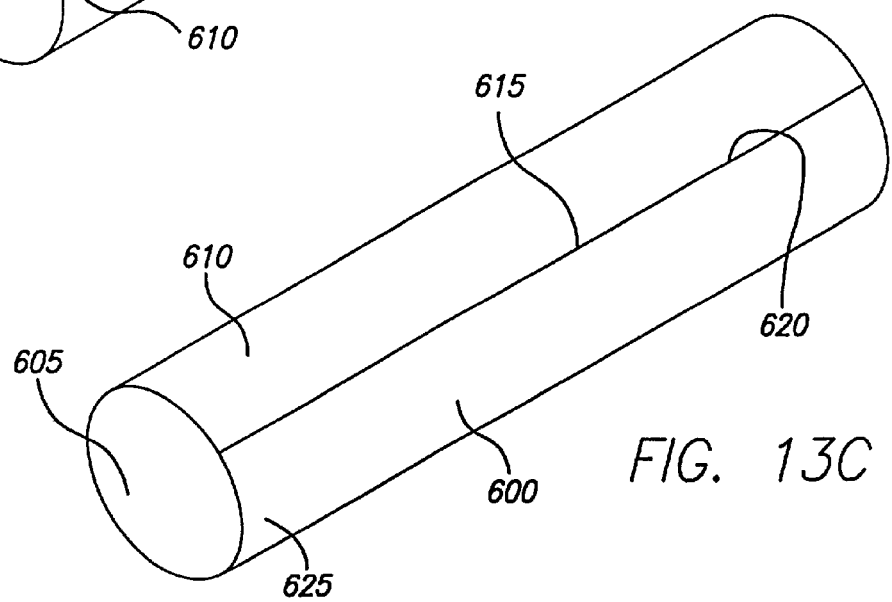

The rough stent form may be in the form of a tubular member, as discussed above and depicted in FIGS. 11A, 11B, 12A, and 12B. Other manufacturing techniques, however, can also be employed to manufacture a stent within the scope of the invention. One such approach starts with a rough stent form comprising a generally planar member 600 having a first side 605 and a second side 610, as depicted in FIG. 13A. Opposing ends 615, 620 of the planar member 600 are brought toward one another, as depicted in FIG. 13B, until they contact one another, depicted in FIG. 13C, so that the planar member 600 forms a tubular shape 625 with the first side 605 forming the inner surface and the second side 610 forming the outer surface. The opposing ends 615, 620, which are now adjacent, can be secured to one another through various methods, such as spotwelding or adhesives.

The above approach can permit the step of varying the thickness to be performed on the generally planar member 600 after it is rolled into a tubular shape. Such steps could be performed in various ways, including the techniques set forth above with respect to the tubular member depicted in FIGS. 11A, 11B, 12A, and 12B. The approach of starting with a generally planar member 600 can also permit the step of varying the thickness to be performed prior to the step of rolling the planar member 600 into a tubular shape 625. For example, material could be selectively thinned from, or added to, the first side 605 of the planar member 600 to vary the thickness of the planar member 600. Thus, when the planar member 600 is rolled into the tubular shape 625, the first side 605, which is the inner surface of the tubular shape 625, will have an uneven surface caused by the differences in thickness. After rolling of the planar member 600, the resulting tubular shape 625 would thus have an uneven inner surface and an uneven outer surface. One advantage to using a generally planar member 600 to form the stent is that the stent pattern may be cut into the planar member 90 prior to or after the planar member 600 is rolled into the tubular shape 625.

Figure 14A:
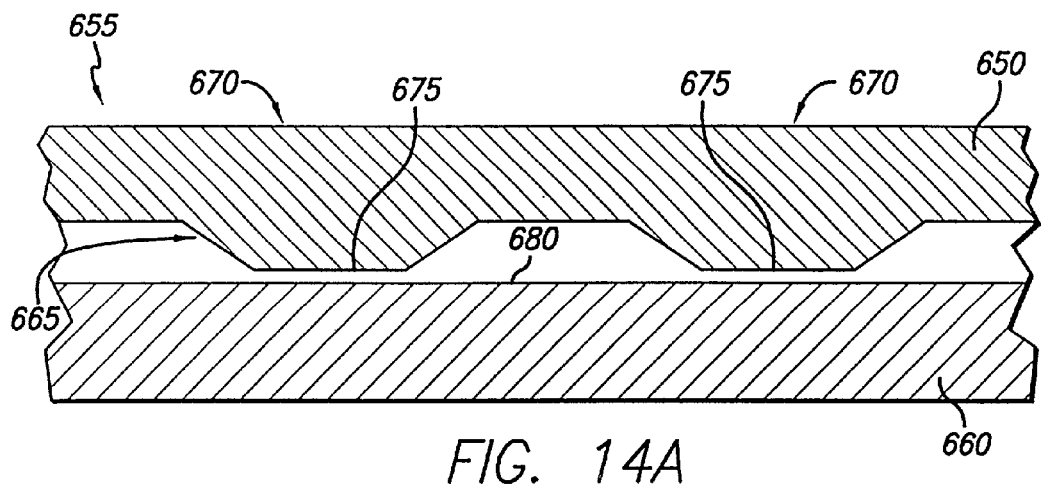
FIGS. 14A and 14B are cross-sectional views of a portion of a stent having grooves formed on the inner surface of the stent in accordance with various embodiments of the present invention shown mounted on a balloon.
Figure 14B:
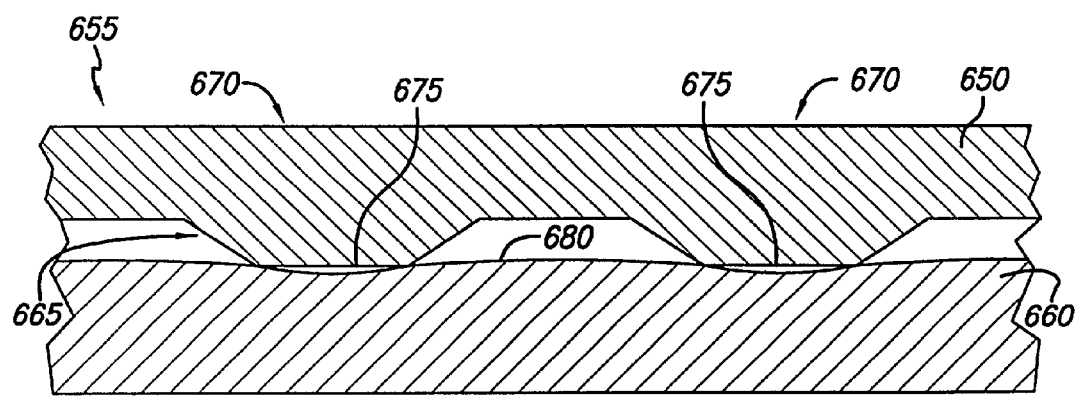

A stent employing embodiments of the present invention such as variable thickness of the stent provided either by adding material to the stent or by forming grooves or other patterns into the inner surface of the stent provide an improved method of retaining a stent onto a balloon. For example, in the embodiment of the present invention depicted in FIG. 14A, a portion 650 of a stent 655 is shown positioned on a balloon 660. The stent inner surface 665 has a varying structure, similar to the embodiments depicted in FIG. 12B, where variable thickness is achieved by varying the surface structure of the inner surface 665. FIG. 14A depicts the stent portion 650 loosely positioned on the balloon 660. FIG. 14B depicts the same stent portion 650 after the stent 655 has been crimped onto the balloon 660. As shown in FIG. 14B, the thicker portions 670 of the stent 655 created inner surface "projections" 675 that, after the stent 655 is crimped onto the balloon 660, press against the balloon surface 680 and help to secure the stent 655 to the balloon 660. Similarly, where asperities are created on selected portions of the inner surface of a stent as described above, the asperities press against the balloon surface, increasing the frictional contact between the stent and the balloon surface, thus helping to secure the stent to the balloon.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the scope of the invention. For example, while the present invention has been described herein in terms of an expandable stent for use within a patient's blood vessel, the invention can also be employed for stents for use within other body lumens. Accordingly, it is not intended that the invention be limited, except as by the appended claims.

What is claimed is:

1. In a combination of an expandable balloon of a stent delivery catheter and a balloon expandable stent mounted on the expandable balloon, the expandable stent having a body portion with an inner surface and an outer surface, and a plurality of asperities including protrusions and indentations formed on the inner surface of the body portion, the improvement comprising:

a friction increasing coating formed on a selected area of the inner surface of the body portion, the friction increasing coating covering the plurality of asperities on said selected area, and the selected area of the inner surface having a roughness factor between approximately 40 nm and approximately 210 nm.

2. The combination of claim 1, wherein the protrusions and indentations have a shape selected from the group of shapes consisting of rounded, pointed and rectangular shapes.

3. The combination of claim 2, wherein the asperities comprise material deposited on the area of the inner surface of the stent that is roughened.

4. The combination of claim 1, wherein the asperities are formed on an area of the stent wherein material has been selectively etched from the stent.

5. The combination of claim 1, wherein the asperities are formed on substantially the entire inner surface of the stent.

6. The combination of claim 1, wherein the stent includes first and second ends and the asperities are formed on a portion of the inner surface of the stent adjacent the first and second ends such that a middle portion of the inner surface of the stent is smooth.

7. The combination of claim 1, wherein the asperities have a roughness factor between approximately 100 nm and approximately 200 nm.

8. The combination of claim 1, wherein the stent includes a wall having a selected thickness defined by the inner and outer surfaces of the stent, and wherein the plurality of asperities are formed on at least one region where the wall is thinner than the selected thickness.

9. The combination of claim 8, further including a groove in the inner surface.

10. The combination of claim 8, wherein the asperities cover substantially the entire inner surface of the stent.

11. The combination of claim 8, wherein the stent further includes a first end and a second end, and wherein the asperities cover selected regions adjacent the first and second ends, the stent also having a middle portion that is substantially smooth.

* * * * *

UNITED STATES PATENT AND TRADEMARK OFFICE
CERTIFICATE OF CORRECTION

PATENT NO. : 6,979,346 B1 Page 1 of 1
DATED : December 27, 2005
INVENTOR(S) : Syed Hossainy et al.

It is certified that error appears in the above-identified patent and that said Letters Patent is hereby corrected as shown below:

Column 3,
Line 34, delete "on a surface of a" and insert -- by adding --.
Lines 63-64, delete "be come" and insert -- become --.

Column 6,
Line 34, delete "fort he" and insert -- for the --.

Column 10,
Line 19, delete "which known" and insert -- which is known --.

Column 12,
Line 7, delete "physically moved" and insert -- physically be moved --.

Signed and Sealed this

Sixth Day of June, 2006

JON W. DUDAS
*Director of the United States Patent and Trademark Office*